United States Patent [19]
Weisman et al.

[11] Patent Number: 6,140,315
[45] Date of Patent: Oct. 31, 2000

[54] THERAPEUTIC USES OF GOSERELIN ACETATE

[76] Inventors: Kenneth M. Weisman, 30 Springton Point Dr., Newtown Square, Pa. 19073; Michael Goldberg, 20 Aspen Dr., Ivyland, Pa. 18974

[21] Appl. No.: 09/089,198

[22] Filed: Jun. 5, 1998

Related U.S. Application Data

[60] Provisional application No. 60/049,169, Jun. 9, 1997.

[51] Int. Cl.⁷ .......................... A61K 31/56; A61K 31/535
[52] U.S. Cl. ...................... 514/177; 514/178; 514/236.2; 514/310; 514/324; 514/428; 514/448; 514/470; 514/565
[58] Field of Search ...................................... 514/177, 178, 514/236.2, 310, 324, 470, 428, 448, 565

[56] References Cited

U.S. PATENT DOCUMENTS

| | | | |
|---|---|---|---|
| 5,770,609 | 6/1998 | Grainger et al. | 514/319 |
| 5,872,114 | 2/1999 | Labrie | 514/178 |
| 5,906,987 | 4/1999 | Chwalisz et al. | 514/177 |

OTHER PUBLICATIONS

Goodman and Gilman's Pharmacological Basis of Therapeutics, pp. 1427–1429, 1980.

*Primary Examiner*—James O. Wilson
*Assistant Examiner*—Howard Owens
*Attorney, Agent, or Firm*—Caesar, Rivise, Bernstein, Cohen & Pokotilow, Ltd.

[57] ABSTRACT

A method of decreasing atherosclerosis and its complications, such as myocardial infarction, stroke and peripheral vascular disease, wherein the method involves administering to a human or an animal an amount of goserelin acetate sufficient to decrease atherosclerosis and its complications.

3 Claims, No Drawings

THERAPEUTIC USES OF GOSERELIN ACETATE

This application claims the benefit of the filing date of Jun. 9, 1997 of Provisional patent application Ser. No. 60/049,169.

BACKGROUND OF THE INVENTION

Goserelin Acetate, a synthetic decapeptide analogue of LHRH or GnRH, is chemically described as an acetate salt of [D-Ser(Bu$^t$)$^6$ Azygly$^{10}$] LHRH. Its chemical structure is pyro-Glu-His-Trp-Ser-Tyr-D-Ser(Bu$^t$)-Leu-Arg-Pro-Azgly-NH2 acetate [C59H84N18O14 (C2H4O2) sold under the trademark Zoladex, as identified by the U.S. Pat. No. 5,510,460, the entire disclosure is incorporated by reference herein, is known for the use in treatment of prostatic carcinoma. Goserelin acetate is known to reduce levels of GnRH or LHRH, and Testosterone, a sex hormone. This process of changing a sex hormone level to produce a desired effect is known as hormonal manipulation.

SUMMARY OF THE INVENTION

The present invention involves the use of Goserelin Acetate in the prevention and treatment of atherosclerosis and its complications including but not limited to coronary artery disease, stroke, and peripheral vascular disease.

DESCRIPTION OF THE PREFERRED EMBODIMENTS

A retrospective study was performed which compared the rates of patient reported heart attack in several groups. 1—control group of males entering the urology office for any routine complaint. 2—a group of prostate cancer patients treated with Leuprolide acetate, a LHRH inhibitor. 3—a group of prostate cancer patients treated with Goserelin acetate, a LHRH inhibitor. 4—a group of prostate cancer patients not treated with hormonal manipulation (neither Leuprolide or Goserelin). 5—all patients on LHRH inhibitors (group 2 + group 3).

The patients on either Leuprolide or Goserelin were treated with the recommended doses indicated for the treatment of prostatic carcinoma, at either one or three month intervals depending on the preparation used. Leuprolide was dosed at 7.5 mg monthly (single intramuscular injection) or at 22.5 mg at 3 month intervals (single intramuscular injection). Goserelin was dosed at 3.6 mg monthly (subcutaneous injection) or at a dose of 10.8 mg at 3 month intervals (subcutaneous injection).

The various groups of office patients were given a questionnaire. In groups 2 and 3 only those on drug for at least one year were considered. Cardiac event is defined either the history of a heart attack or occurrence of coronary artery bypass or angioplasty. In control groups only events occurring in the 3 years prior to the questionnaire are charted. The results were as follows:

|  | No Patients | Cardiac Events | Subject Years | Events/Year |
|---|---|---|---|---|
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 (Lupron) | 28 | 1 | 118 | .00847 |
| Group 3 (Goserelin) | 25 | 1 | 62 | .0161 |
| Group 6 (antiLHRH) groups 2 + 3 | 50 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (Lupron) and Total Control is 0.253. 95% Confidence Interval for the difference between the proportions is 0.00514 and 0.0454. Patients treated with Leuprolide acetate had fewer heart attacks than controls.

The observed difference between the proportions of Group 3 and Total Control is 0.0177. Patients treated with Goserelin had fewer heart attacks than controls.

Without further elaboration the foregoing will so fully illustrate our invention that others may, by applying current and future knowledge, adopt the same for use under various conditions of service.

What is claimed is:

1. A method of decreasing atherosclerosis, myocardial infarction and peripheral vascular disease comprising administering to a human or animal an amount of Goserelin acetate sufficient to decrease atherosclerosis and its complications.

2. The method in claim 1 wherein the effective amount of Goserelin is a 3.6 mg subcutaneous implant administered monthly.

3. The invention in claim 1 wherein Goserelin is administered as a tablet, or as part of a liquid solution or dispersion, or patch, or subcutaneous pellet, with the intent of accomplishing systemic absorption or the drug.

* * * * *